United States Patent
Warner et al.

(10) Patent No.: US 8,759,576 B2
(45) Date of Patent: Jun. 24, 2014

(54) PROCESSES FOR PURIFYING ACETIC ANHYDRIDE

(75) Inventors: R. Jay Warner, Houston, TX (US);
Melchoir Meilchen, Houston, TX (US);
Nathan Kirk Powell, Waxahachie, TX (US)

(73) Assignee: Celanese International Corporation, Irving, TX (US)

( * ) Notice: Subject to any disclaimer, the term of this patent is extended or adjusted under 35 U.S.C. 154(b) by 13 days.

(21) Appl. No.: 13/605,278

(22) Filed: Sep. 6, 2012

(65) Prior Publication Data

US 2014/0066653 A1   Mar. 6, 2014

(51) Int. Cl.
*C07C 51/573* (2006.01)
*C07C 53/12* (2006.01)

(52) U.S. Cl.
CPC ................................... *C07C 53/12* (2013.01)
USPC ...................................................... 562/898

(58) Field of Classification Search
CPC combination set(s) only.
See application file for complete search history.

(56) References Cited

U.S. PATENT DOCUMENTS

| | | | | |
|---|---|---|---|---|
| 2,743,296 | A | * | 4/1956 | Painter et al. ................. 562/892 |
| 4,046,807 | A | | 9/1977 | Kuckertz |
| 4,107,002 | A | * | 8/1978 | Eck et al. ......................... 203/75 |
| 4,333,884 | A | | 6/1982 | Kubbeler et al. |
| 4,497,747 | A | | 2/1985 | Vogt et al. |
| 5,264,087 | A | * | 11/1993 | Lowery et al. .................. 203/80 |
| 5,370,774 | A | | 12/1994 | Kuenstle et al. |
| 5,380,929 | A | | 1/1995 | Erpenbach et al. |
| 5,648,531 | A | | 7/1997 | Morimoto et al. |
| 7,199,263 | B2 | | 4/2007 | Warner |

OTHER PUBLICATIONS

International Search Report and Written Opinion for PCT/US2013/056336 mailed Jan. 9, 2014.

* cited by examiner

*Primary Examiner* — Karl J Puttlitz (57) ABSTRACT

In one embodiment, the invention is to a process for purifying acetic anhydride. The process includes the steps of feeding a liquid crude acetic anhydride stream directly to a distillation column and separating the liquid crude acetic anhydride stream to produce a light ends stream, a sidedraw and a residue stream. The sidedraw comprises substantially pure acetic anhydride product. The distillation column is operated at a pressure less than 101 kPa. The substantially pure acetic anhydride product comprises greater than 98 wt. % acetic anhydride, has a permanganate time of greater than 10 minutes, and has an APHA color of less than 10.

28 Claims, 1 Drawing Sheet

PROCESSES FOR PURIFYING ACETIC ANHYDRIDE

FIELD OF THE INVENTION

The present invention relates generally to the production of acetic anhydride. More specifically, the present invention relates to the production of crude acetic anhydride via the reaction of acetic acid and ketene and to the separation of the crude acetic anhydride.

BACKGROUND OF THE INVENTION

Acetic anhydride is a clear, colorless, liquid with a sharp, vinegar-like odor. Acetic anhydride is a commercially valuable chemical and can be found in a wide variety of industrial applications. Some primary applications of acetic anhydride include its use in the manufacture of cellulose acetate for films, plastic goods and coatings. Other applications include use in the manufacture of perfumes, explosives, synthetic fibers, sweeteners, polymers (e.g., polyoxytetramethylene glycol and polyacetal), weed killers, fungicides, various industrial chemicals, acetylsalicylic acid (aspirin), acetylcholine hydrochloride, acetophenacetin, sulfonamides, aceto-p-aminophenol, cortisone, acetanilide, theophylline, sulfa drugs, certain vitamins and hormones, and many other various pharmaceuticals and pharmaceutical intermediates not listed here. Acetic anhydride can also be used in the chemical treatment of papers and textiles and to produce acetyl ricinoleates, triacetin, acetyl tributyl citrate, and other plasticizers. Because acetic anhydride reacts with water, it is also sometimes used as a dehydrating agent in reaction mixtures where the removal of water is necessary.

Acetic anhydride may be prepared via the reaction of acetic acid and ketene. Ketene, a valuable intermediate for the synthesis of many organic compounds, may be prepared by the thermal decomposition (continuous cracking) of acetic acid in the presence of a catalyst, e.g., triethyl phosphate. This reaction may be conducted at temperatures at or above 600° C. and under pressures ranging from about 10 kPa to 50 kPa. Ammonia may be added to the mixture of hot cracked gas shortly after it leaves the reaction zone to neutralize the catalyst. Ketene is then isolated from the cracked gas and reacted with excess acetic acid to obtain crude acetic anhydride.

Typically, the ketene/acetic acid reaction is carried out in a system which includes an absorber and a scrubber. The majority of the ketene is reacted in the absorber stage. A crude acetic anhydride product stream exits the bottom of the absorber. Residual ketene, e.g., unreacted ketene, exits the absorber stage (via an overhead gas stream) and is typically directed to the scrubber to convert the unreacted ketene into additional acetic anhydride.

Various processes are known for purifying crude acetic anhydride. One conventional process requires the use of three columns, and, as such, necessitates a large capital expenditure. Attempts have been made to reduce the expenditure by reducing the number of columns. For example, U.S. Pat. No. 4,107,002 discloses the use of evaporators to evaporate the crude acetic anhydride into one portion comprising gaseous distillable components and another portion consisting substantially of non-gaseous non-distillable components. The gaseous distillable components are fed to a single distillation column to recover acetic anhydride at the lower part of the column. This separation scheme, however, requires at least one evaporator, which adds to both capital and operating expenditures.

Notwithstanding the above, there remains a need for a process for purifying acetic anhydride which eases the burden of capital expenditures associated with existing processes, and provides a high purity acetic anhydride.

BRIEF DESCRIPTION OF DRAWINGS

The invention is described in detail below with reference to the appended drawings, wherein like numerals designate similar parts.

SUMMARY OF THE INVENTION

In one embodiment, the invention relates to a process for purifying acetic anhydride. The process comprises the step of feeding a liquid crude acetic anhydride stream directly to a distillation column. The process further comprises the step of separating the liquid crude acetic anhydride stream to produce a light ends stream, a sidedraw and a residue stream. Preferably, the sidedraw comprises substantially pure acetic anhydride product. In one embodiment, the pressure of the distillation column is less than 101 kPa. Preferably, the substantially pure acetic anhydride product comprises greater than 98 wt. % acetic anhydride, has a permanganate time of greater than 10 minutes, and has an APHA color of less than 10.

In another embodiment, the process comprises the step of contacting ketene gas with acetic acid in an absorber column to produce a liquid crude acetic anhydride stream and a residue ketene stream. The process further comprises the steps of feeding the liquid crude acetic anhydride stream directly to a distillation column and purifying the liquid crude acetic anhydride stream to product a light ends stream, a substantially pure acetic anhydride product, and a residue stream. In one embodiment, the substantially pure acetic anhydride product is withdrawn as a sidedraw from the distillation column. Preferably, the pressure of the distillation column is greater than 20 kPa. Preferably, the substantially pure acetic anhydride product stream is as discussed above.

In another embodiment, the process comprises the step of feeding a liquid crude acetic anhydride stream directly to a distillation column. Preferably, the distillation column operates at a pressure less than 101 kPa and at a temperature less than 150° C.

DETAILED DESCRIPTION OF THE INVENTION

Introduction

The purification of crude acetic anhydride via the reaction between acetic acid and ketene is typically carried out in multi-column systems, e.g., three column systems, or systems using one or more evaporators in conjunction with one or more columns. Unfortunately, the capital and operating expenditure for these systems is high because the number of separation units required by these systems.

Surprisingly and unexpectedly, it has now been discovered that acetic anhydride product of suitable purity may be recovered from crude acetic anhydride by using only a single distillation column. In preferred embodiments, the distillation column is operated at a lower pressure, e.g., a pressure less than 101 kPa, less than 91 kPa, or less than 80 kPa. The separation produces a light ends stream, a sidedraw and a residue stream. Surprisingly and unexpectedly, when the column is operated at this lower pressure, substantially pure acetic anhydride product may be withdrawn as a sidedraw from the distillation column without the need for additional purification. Typically, one or more separation units, e.g., evaporators in combination with distillation columns, are used to purify crude acetic anhydride. Unlike previous processes, the process of the present invention utilizes a single distillation column without any additional separation units, e.g, evaporators and/or distillation columns, to obtain substantially pure acetic anhydride. Specifically, the process of the present invention directly feeds liquid crude acetic anhydride product to a distillation column. Thus, the requirement of one or more additional separation units, e.g., evaporators and/or columns, is beneficially eliminated. In one embodiment, the substantially pure acetic anhydride product has a high permanganate time and/or a low APHA color value, e.g., as measured under ASTM D1209 or other analytical methods.

In one embodiment, the present invention relates to a process for purifying acetic anhydride. The inventive process comprises the step of feeding a liquid crude acetic anhydride stream directly to a distillation column. In a preferred embodiment, the liquid crude acetic anhydride stream is separated to produce a light ends stream, a sidedraw and a residue stream. The sidedraw comprises substantially pure acetic anhydride product. For example, the substantially pure acetic anhydride product, e.g., the sidedraw, may comprise greater than 98 wt. % acetic anhydride, e.g., greater than 99 wt. %, or greater than 99.5 wt. %. In one embodiment, the substantially pure acetic anhydride product has a permanganate time of greater than 10 minutes, e.g., greater than 30 minutes, or greater than 50 minutes. In one embodiment, the substantially pure acetic anhydride product has an APHA color of less than 10, e.g., less than 8, or less than 5.

In an embodiment, the crude liquid acetic anhydride is fed at the top portion of the distillation column, e.g., the top half or the top third. In an embodiment, the substantially pure acetic anhydride product is withdrawn at the lower portion of the distillation column, e.g., lower half, or the lower third. In a preferred embodiment, the substantially pure acetic anhydride product is withdrawn from a point of the distillation column that is below the point at which the liquid crude anhydride stream is fed. Without being bound by theory, it is believed that light end impurities in the liquid crude anhydride stream are removed in the overhead of the distillation column. As such, light end impurities may potentially contaminate a product stream that is withdrawn above the point at which the crude stream is fed. Accordingly, by withdrawing the substantially pure acetic anhydride product in accordance with the present invention, a highly pure acetic anhydride product may be obtained. In a preferred embodiment, the distillation column is operated at the low pressures discussed above. The inventors have discovered that by reducing the pressure of the distillation column, substantially pure acetic anhydride may be recovered from the sidedraw of the distillation column. Without being bound by theory, it is believed that the reduction of the distillation column pressure allows the column to operate at lower temperatures. As such, thermal decomposition of acetic anhydride stream is reduced or eliminated, which reduces impurity formation and improves overall acetic anhydride production.

In one embodiment, the residue stream comprises acetic anhydride and non-distillables. For example, the non-distillables may include higher boiling point anhydrides, catalyst derivatives, and polymers. In one embodiment, the residue stream comprises at least 90 wt. % acetic anhydride, e.g., at least 92 wt. % acetic anhydride, or at least 95 wt. % acetic anhydride. The residue stream may further comprise other components, as discussed below.

In one embodiment, at least a portion of the residue stream may be fed to a heavy ends removal system to produce a recovered acetic anhydride stream and a high solids content stream. The high solids content stream may be removed from the acetic anhydride removal system. The recovered acetic anhydride stream comprises additional acetic anhydride. Preferably, the recovered acetic anhydride stream comprises a higher concentration of acetic anhydride than the residue stream. For example, the recovered acetic anhydride stream may comprise at least 95 wt. % acetic anhydride, e.g., at least 96 wt. % or at least 97 wt. %. The recovered acetic anhydride stream may further comprise other components, which are discussed below. At least a portion of the recovered recycled acetic anhydride stream may be fed to the distillation column, directly or indirectly, to recover substantially pure acetic anhydride in the sidedraw. In one embodiment, the recovered acetic anhydride steam may be combined with the crude acetic anhydride before being fed to the distillation column. In one embodiment, the recovered acetic anhydride may be fed directly to distillation column, e.g., without being combined with the crude acetic anhydride. Preferably, the recovered acetic anhydride is fed at a point of the distillation column that is between the point at which the crude acetic anhydride is fed and the point at which the sidedraw is withdrawn. In an embodiment, the recovered acetic anhydride is returned to a point of the distillation column where the composition of the recovered acetic anhydride matches the tray compositions of the distillation column.

In one embodiment, the crude acetic anhydride stream is formed by contacting, e.g., reacting, acetic acid and ketene. Preferably, the acetic acid and ketene are reacted in an absorber column. The contacting yields the crude acetic anhydride product stream and a vent stream comprising residual, unreacted ketene. In one embodiment, the acetic acid reactant is formed by carbonylating methanol and/or a methanol derivative with carbon monoxide to form the acetic acid. In one embodiment, the ketene that is used as a reactant may be formed by pyrolyzing acetic acid in a cracking furnace. After separation of the ketene gas from a liquid stream comprising water and acetic acid, the ketene gas is contacted with liquid acetic acid to produce the crude acetic anhydride product stream and the vent stream. In one embodiment, the vent stream may comprise from 0.1 wt. % to 10 wt. % (residual) ketene, e.g., from 0.1 wt. % to 8 wt. % or from 1 wt. % to 5 wt. %. In preferred embodiments, at least a portion of the unreacted ketene is directed to a liquid ring vacuum compressor, which comprises a ring seal fluid comprising acetic acid. Preferably, the process does not employ a ketene scrubber and the unreacted ketene is fed directly to the liquid ring vacuum compressor, although, in some embodiments, the unreacted ketene may be directed through heat exchanger equipment and/or additional pumping equipment before reaching the liquid ring vacuum compressor. In some embodiments, surprising ketene conversions are achieved when the ring seal fluid comprises specific concentrations of acetic acid. In one embodiment, the acetic acid acts as both a seal fluid and a reactant in the liquid ring vacuum compressor in embodiments of the present disclosure. Preferably, the unreacted ketene is contacted with the ring seal fluid to form additional acetic anhydride, e.g., a supplemental acetic anhydride product. As a result, the overall conversion of ketene to acetic anhydride of the inventive process is at least 95%, e.g., at least 97%, at least 98%, at least 99%, at least 99.5%, or at least 99.99%.

Acetic Acid

As noted above, in one embodiment, the inventive process includes the step of carbonylating methanol and/or a methanol derivative with carbon monoxide to form acetic acid. As used herein, the term "methanol derivative" refers to a compound that is derived from or formed from methanol. Examples of methanol derivatives include, but are not limited to, methyl acetate and dimethyl ether. The carbonylation of methanol proceeds according to the following equation:

The acetic acid used in connection with the process of this invention may be derived from any suitable source including natural gas, petroleum, coal, biomass, and so forth. In one embodiment, the acetic acid may be produced via methanol carbonylation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes,* and in particular, species selected from the group consisting of *Clostridium formicoaceticum, Clostridium butyricum, Moorella thermoacetica, Thermoa-naerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

In one optional embodiment, the acetic acid that is utilized in the acetic acid/ketene reaction comprises acetic acid and may also comprise other carboxylic acids, e.g., propionic acid, esters, and anhydrides, such as acetic anhydride, as well as acetaldehyde. In one embodiment, the acetic acid fed to the acetic acid/ketene reaction comprises "light-end" impurities, such as acetone and acetonitrile. In another embodiment, the acetic acid fed to the acetic acid/ketene reaction comprises propionic acid. For example, the acetic acid fed to the reaction may comprise less than 600 ppm propionic acid, e.g., less than 590 ppm, less than 575 ppm, less than 500 ppm, less than 400 ppm, or less than 300 ppm propionic acid in the acetic acid feed. The acetic acid fed to the reaction may be a cruder acetic acid feed stream, e.g., a less-refined acetic acid feed stream.

In one embodiment, acetic acid in vapor form may be taken directly as crude product from the flash vessel of a methanol carbonylation unit of the class described in U.S. Pat. No. 6,657,078, the entirety of which is incorporated herein by reference.

In another embodiment, at least a portion of the acetic acid that is fed to the acetic acid/ketene reaction may be provided by a recycle stream. For example, excess acetic acid that is fed to the acetic acid/ketene reaction may be recovered from the crude acetic anhydride product stream through various separation steps. The recovered acetic acid is then fed to the acetic acid/ketene reaction as a recycle stream. The acetic acid stream may comprise low amounts of acetic anhydride, and/or low amounts of water. In optional embodiments, the acetic acid recycle stream may further comprise impurities that are more volatile (i.e. have lower boiling points) that acetic anhydride. In such optional embodiments, the inventive process may comprise additional steps for purging these lower boiling point ("light-ends") impurities from the recycle stream. Although these impurities do not affect the acetic acid/ketene reaction, they may have an effect on the overall quality of the acetic anhydride product.

In another embodiment, the acetic acid or acetic/acetic anhydride mixtures used in the acetic acid/ketene reaction may be derived from an acetylation processes involving acetic anhydride. Examples of such acetylation processes include those used in processes relating to pharmaceuticals, food additives, poly-THF, and cellulose acetylation.

Ketene

Ketene can be prepared by various methods known in the art, most commonly by vapor phase pyrolysis (continuous cracking) of acetic acid in the presence of a catalyst at subatmospheric pressure. Suitable pyrolysis catalysts include, but are not limited to, triethyl phosphate, diammonium phosphate, monoammonium phosphate or other esters of phosphoric acid. In one embodiment, the pyrolysis catalyst may be added in an amount ranging from 0.1 to 0.5 wt. % based on total weight of the feed. In some embodiments of the present invention, the pyrolysis is conducted at temperatures at or above 600° C., such as 650° C., 700° C., 750° C., 800° C., 850° C., 880° C., 900° C., 950° C. or 1100° C. In terms of ranges, the pyrolysis may be conducted at a temperature ranging from 600° C. to 1100° C., e.g., from 650° C. to 1000° C., from 700° C. to 1000° C., from 725° C. to 990° C., or from 740° C. to 900° C. In preferred embodiments, the pyrolysis is conducted at a temperature ranging from 600° C. to 650° C. In one embodiment, a neutralizing agent, such as ammonia, may be introduced to the reactor system after pyrolysis to neutralize the pyrolysis catalyst. The neutralizing agent also acts to retard recombination of the ketene with reacted acetic acid, and/or water formed during the reaction. Suitable neutralizing agents include, but are not limited to, ammonia, pyridine, aniline, or other suitable aliphatic amines.

In order to recover ketene by purification of the pyrolysis gas, condensable gas may be separated from the pyrolysis gas. Accordingly, in one embodiment of the present invention, the pyrolysis gas is rapidly cooled, and the ketene gas is recovered by separating the condensable component(s), e.g., $H_2O$, acetic acid, etc., from the pyrolysis gas. In embodiments where it is desired, the ketene gas may be further cooled by use of one or more condensers to, for example, 10° C. or less, to remove all but trace quantities of water and acetic acid from the recovered ketene.

Primary Reaction and Separation

As noted above, the inventive process, in one embodiment, further comprises the step of contacting ketene with acetic acid to produce a crude acetic anhydride product stream and a vent stream. In preferred embodiments, this step is performed in an absorber column. Ketene, in the vapor phase, and acetic acid, in the liquid phase, may be fed to the absorber column.

In one embodiment, the crude acetic anhydride product stream of the present invention comprises a significant portion of acetic anhydride. For example, the crude product stream may comprise at least 50 wt. % acetic anhydride, e.g., at least 75 wt. %, at least 80 wt. %, at least 85 wt. %, at least 90 wt. %, or at least 95 wt. %. In terms of ranges, the crude product stream may comprise from 1 wt. % to 95 wt. % acetic anhydride, e.g., from 15 wt. % to 60 wt. %, from 25 wt. % to 75 wt. %, from 30 wt. % to 80 wt. %, from 50 wt. % to 85 wt. %, from 60 wt. % to 85 wt. %, from 70 wt. % to 85 wt. %, or from 75 wt. % to 95 wt. %. In terms of upper limits, the crude product stream may comprise less than 95 wt. % acetic anhydride, e.g., less than 90 wt. % acetic anhydride, less than 85 wt. % acetic anhydride, less than 80 wt. % acetic anhydride, or less than 75 wt. % acetic anhydride. The crude product stream may be further purified, as discussed herein. In one embodiment, the crude product stream may be combined with acetic anhydride from the secondary reaction and the combined stream may be further purified.

In one embodiment, the crude acetic anhydride product stream of the present invention further comprises acetic acid. For example, the crude product stream may comprise at least 1 wt. % acetic acid, at least 3 wt. % acetic acid, or at least 5 wt. % acetic acid. In terms of ranges, the crude product stream may comprise from 1 wt. % to 25 wt. % acetic acid, from 5 wt. % to 25 wt. %, from 3 wt. % to 20 wt. % acetic acid, or from 5 wt. % to 15 wt. % acetic acid. In terms of upper limits, the crude product stream of the present invention may comprise less than 25 wt. % acetic acid, e.g., less than 20 wt. % acetic acid, less than 15 wt. % acetic acid, less than 10 wt. % acetic acid, or less than 5 wt. % acetic acid.

In other embodiments, the crude acetic anhydride product stream may comprise propionic acid, acetic acid, acetic-propionic anhydride, propionic anhydride, acetaldehyde, acetone, diketene, acetamide, diacetamide, acetonitrile, ethylidene diacetate, 1,1-methanediol diacetate, acetaldehyde, and mixtures thereof. Although the acetic acid feed and the ketene gas stream may contain very small concentrations of water, the crude acetic anhydride stream preferably does not contain measureable amounts of water.

In some embodiments, at least a portion of the crude acetic anhydride product stream may be hydrogenated to ethanol.

Exemplary compositional data for the crude product stream are shown in Table 1. Components other than those listed in Table 1 may also be present in the crude product stream.

TABLE 1

| CRUDE ACETIC ANHYDRIDE PRODUCT STREAM | | | | |
|---|---|---|---|---|
| Component | Conc. (wt. %) | Conc. (wt. %) | Conc. (wt. %) | Conc. (wt. %) |
| Acetic Anhydride | 1 to 95 | 10 to 85 | 10 to 90 | 15 to 95 |
| Acetic Acid | 0.1 to 20 | 1 to 10 | 1 to 15 | 1 to 20 |
| Propionic Acid | 0.001 to 1 | 0.01 to 1 | 0.1 to 2 | 0.01 to 0.1 |
| Acetic-Propionic Anhydride | 0.001 to 1 | 0.01 to 1 | 0.1 to 2 | 0.01 to 0.1 |

As discussed above, the crude acetic anhydride product stream may be separated in a single distillation column to form a purified product, e.g., the substantially pure acetic anhydride product. In one embodiment, the separation of the crude acetic anhydride does not involve any separation units other than the distillation column, e.g., an evaporator and/or a column in addition to the distillation column. In one embodiment, the inventive process comprises the step of separating the crude acetic anhydride product stream into a light ends stream, a sidedraw and a residue stream. The distillate stream may comprise light ends components. For example, the distillate stream may comprise acetic acid, propionic acid, acetone, diketene, or acetaldehyde, acetonitrile. In one embodiment, the distillate stream may be recycled to the primary reaction zone to make additional acetic anhydride. In other embodiments, the distillate stream may be removed from the purification process or recycled to other reaction systems.

In one embodiment, the sidedraw comprises substantially pure acetic anhydride product. For example, the sidedraw may comprise greater than 98 wt. % acetic anhydride, e.g., greater than 99.0 wt. % or greater than 99.5 wt. %. In terms of upper limits, the sidedraw of the present invention may comprise at most 99.99 wt. % acetic anhydride, e.g., at most 99.95 wt. % or at most 99.9 wt. %. In terms of ranges, the sidedraw of the present invention may comprise from 98 wt. % to 99.99 wt. % acetic anhydride, e.g., from 99.0 wt. % to 99.9 wt. %, or from 99.5 wt. % to 99.95 wt. %.

In one embodiment, the residue may comprise an amount of acetic anhydride. In one embodiment, the residue may comprise acetic acid, propionic acid, acetone, diketene, or acetaldehyde, acetonitrile. Preferably, the residue may comprise at least 90 wt. % acetic anhydride, e.g., at least 92 wt. %, or at least 95 wt. %. In terms of upper limits, the residue may comprise at most 99 wt. % acetic anhydride, e.g., at least 98 wt. %, or at most 97 wt. %. In terms of ranges, the residue may comprise from 90 wt. % to 99 wt. % acetic anhydride, e.g., from 92 wt. % to 98 wt. %, or from 95 wt. % to 97 wt. %. The compositions of the sidedraw and the residue stream are discussed in further detail below.

In one embodiment, the inventors have found that by operating the distillation at a reduced pressure, substantially pure acetic anhydride may be recovered from the sidedraw without additional purification. In one embodiment, the distillation column may be operated at a pressure from about 20 kPa to 101 kPa, e.g., from about 27 kPa to 93 kPa or from about 33 kPa to 87 kPa. In terms of lower limits, the distillation may be carried out at a pressure greater than 20 kPa, e.g., greater than 27 kPa or greater than 33 kPa. In terms of upper limits, the distillation may be carried out at a pressure less than 101 kPa, e.g., less than 93 kPa or less than 87 kPa. In one embodiment, the pressure in the top portion of the distillation column may be from 20 kPa to 87 kPa, e.g., from 27 kPa to 80 kPa, or from 33 kPa to 73 kPa. In terms of lower limits, the pressure in the top portion of the distillation column may be greater than 20 kPa, e.g., greater than 27 kPa, or greater than 33 kPa. In terms of upper limits, the pressure in the top portion of the distillation column may be less than 87 kPa, e.g., less than 80 kPa or less than 73 kPa.

In one embodiment, the pressure in the top portion of the distillation column may be different than the pressure in the bottom portion of the column. In one embodiment, the pressure in the bottom portion of the distillation column may be higher than in the top portion of the distillation column. In one embodiment, the pressure in the bottom portion of the distillation column may be from 25 kPa to 110 kPa, e.g., from 40 kPa to 90 kPa, or from 55 kPa to 75 kPa. In terms of lower limits, the pressure in the bottom portion of the distillation column may be greater than 25 kPa, e.g., greater than 30 kPa, or greater than 50 kPa. In terms of upper limits, the pressure in the bottom portion of the distillation column may be less than 110 kPa, e.g., less than 90 kPa or less than 75 kPa.

In one embodiment, the liquid crude acetic anhydride stream is heated prior to being distilled. In an embodiment, the liquid crude acetic anhydride stream is heated to a temperature from 40° C. to 120° C., e.g., from 50° C. to 115° C. or from 60° C. to 100° C. In one embodiment, the base of the distillation column may be operated at a temperature from 100° C. to 150° C., e.g., from 110° C. to 140° C., or from 115° C. to 135° C. In terms of upper limits, the distillation column may be operated at a temperature less than 150° C., e.g., less than 140° C., or less than 135° C. In terms of lower limits, the distillation column may be operated at a temperature greater than 100° C., e.g., greater than 110° C., or greater than 115° C.

In one embodiment, the crude acetic anhydride may be fed to the distillation at a point higher than the point at which the sidedraw is withdrawn. In one embodiment, the crude acetic anhydride may be fed to the distillation column at the top part of the column, e.g., top half or top third. In one embodiment, the sidedraw may be withdrawn from the distillation at the bottom part of the column, e.g., bottom half or bottom third.

In one embodiment, the substantially pure acetic anhydride product has a permanganate time of greater than 10 minutes, e.g., greater than 30 minutes, or greater than 60 minutes. In terms of upper limits, the substantially pure acetic anhydride has a permanganate time of less than 90 minutes, e.g., less than 80 minutes, or less than 70 minutes. In terms of ranges, the substantially pure acetic anhydride has a permanganate time of between 10 minutes and 90 minutes, e.g., between 30 minutes and 80 minutes, or between 50 minutes to 70 minutes.

In one embodiment, the substantially pure acetic anhydride product has an APHA color of less than 10, e.g., less than 8, or less than 5. In terms of lower limits, the substantially pure acetic anhydride has an APHA color of greater than 1, e.g., greater than 3, or greater 4. In terms of ranges, the substantially pure acetic anhydride has an APHA color between 1 and 10, e.g., between 3 and 8, or between 4 and 5.

Exemplary compositional data for the distillation column are shown below in Table 2. Components other than those listed in Table 2 may also be present in the streams.

TABLE 2

DISTILLATION COLUMN COMPOSITIONS

| | Conc. (wt. %) | Conc. (wt. %) | Conc. (wt. %) |
|---|---|---|---|
| Distillate Stream | | | |
| Acetic Anhydride | >0.01 | 0.01 to 15 | 1 to 10 |
| Acetic Acid | >60 | 75 to 99 | 85 to 98 |
| Light Ends | >0.01 | >0.05 | 0.1 to 5 |
| Others | >0.01 | >0.1 | >1 |
| Sidedraw | | | |
| Acetic Anhydride | >60 | >80 | 90 to 99.5 |
| Acetic Acid | >0.01 | 0.01 to 15 | 0.1 to 10 |
| Light Ends | >0.01 | >0.01 | 0.01 to 1 |
| Others | >0.01 | >0.01 | 0.01 to 0.1 |
| Residue Stream | | | |
| Acetic Anhydride | >60 | 80 to 99.5 | 90 to 98 |
| Acetic Acid | >0.01 | 0.01 to 10 | 0.1 to 5 |
| Heavy Ends | >0.01 | >0.01 | 0.1 to 10 |
| Others | >0.01 | >0.01 | 0.01 to 1 |

In an embodiment, acetic anhydride in the residue stream may be recovered and returned to the distillation column to recover substantially pure acetic anhydride in the side draw. In one embodiment, the residue stream may comprise of low concentration of heavy ends components. For example, the residue stream may comprise less than 10 wt. % heavy ends components, e.g., less than 5 wt. %, or less than 1 wt. %.

In one embodiment, the heavy ends components may be removed from the residue stream. In one embodiment, a portion of the residue stream may be fed to a heavy ends removal system to produce a recovered acetic anhydride stream and a heavy ends stream. Preferably, the recovered acetic anhydride stream comprises a higher concentration of acetic anhydride than the residue stream. In an embodiment, the recovered acetic anhydride stream comprises at least 95 wt. % acetic anhydride, e.g., at least 96 wt. % or at least 97 wt. %. In terms of upper limits, the recovered acetic anhydride comprise at most 99.5 wt. % acetic anhydride, e.g., at most 99 wt. %, or at most 98 wt. %. In terms of ranges, the recovered acetic anhydride stream comprises from 95 wt. % to 99.5 wt. % acetic anhydride, e.g., from 96 wt. % to 99 wt. %, or from 97 wt. % to 98 wt. %. Preferably, the recovered acetic anhydride stream is substantially free of heavy ends components, e.g., less than 5 wt. %, or less than 3 wt. %. In one embodiment, the heavy ends components in the residue stream may be removed in one or more distillation columns. In one embodiment, the heavy ends components may be removed from the purification process. In some cases, the heavy ends components may be used for fuel, e.g., coal-fired boiler.

In one embodiment, the recovered acetic anhydride stream may be returned to the distillation column directly or indirectly. In one embodiment, the recovered acetic anhydride stream is combined with the crude acetic anhydride before feeding to the distillation column. In another embodiment, the recovered acetic anhydride stream may be returned to the distillation column directly. Preferably, the recovered acetic anhydride stream is returned to a point between the crude acetic anhydride and the sidedraw.

Exemplary compositional data for the heavy ends removal system are shown below in Table 3. Components other than those listed in Table 3 may also be present in the streams.

TABLE 3

HEAVY ENDS REMOVAL SYSTEMS COMPOSITIONS

|  | Conc. (wt. %) | Conc. (wt. %) | Conc. (wt. %) |
| --- | --- | --- | --- |
| Recovered Stream | | | |
| Acetic Anhydride | >60 | 70 to 99 | 80 to 98 |
| Acetic Acid | >1 | 1 to 30 | 2 to 20 |
| Heavy Ends | >0.01 | 0.01 to 15 | 1 to 10 |
| Others | >0.01 | 0.01 to 10 | 0.1 to 5 |
| Heavy Ends Stream | | | |
| Acetic Anhydride | 0.1 to 20 | 1 to 15 | 2 to 10 |
| Acetic Acid | 0.1 to 20 | 1 to 15 | 2 to 10 |
| Heavy Ends | >60 | 60 to 99 | 70 to 95 |
| Others | >0.01 | 0.01 to 10 | 0.1 to 5 |

Returning to the absorber column, the vent stream comprises unreacted ketene. For example, the vent stream may comprise from 0.1 wt. % to 10 wt. % ketene, e.g., from 0.1 wt. % to 8 wt. %, from 0.5 wt. % to 7 wt. %, from 0.75 wt. % to 6 wt. %, or from 1 wt. % to 5 wt. % ketene. In terms of upper limits, the vent stream of the present invention comprises less than 10 wt. % ketene, e.g., less than 9 wt. % ketene, less than 8 wt. % ketene, less than 7 wt. % ketene, less than 6 wt. % ketene, or less than 5 wt. % ketene in the vent stream. In terms of lower limits, the vent stream of the present invention comprises at least 0.1 wt. % ketene, e.g., at least 0.5 wt. % ketene, at least 1 wt. % ketene, at least 2 wt. % ketene, at least 3 wt. % ketene, or at least 5 wt. % ketene in the vent stream.

In one embodiment, the vent stream further comprises acetic acid and/or acetic anhydride, optionally in the vapor phase. For example, the vent stream of the present invention may comprise acetic acid and/or acetic anhydride in an amount ranging from 10 wt. % to 60 wt. %, e.g., from 20 wt. % to 50 wt. %, from 25 wt. % to 45 wt. %, or from 30 wt. % to 40 wt. %. In terms of upper limits, the vent stream of the present invention may comprise less than 40 wt. % acetic acid and/or acetic anhydride, e.g., less than 60 wt. %., less than 50 wt. %, less than 45 wt. %, or less than 40 wt. % acetic acid and acetic anhydride vapor. In terms of lower limits, the vent stream of the present invention may comprise at least 10 wt. % acetic acid and/or acetic anhydride, e.g., at least 20 wt. %, at least 25 wt. %, at least 30 wt. %, or at least 35 wt. %.

Exemplary compositional data for the vent stream are shown below in Table 4. Components other than those listed in Table 4 may also be present in the vent stream.

TABLE 4

VENT STREAM COMPOSITIONS

| Component | Conc. (wt. %) | Conc. (wt. %) | Conc. (wt. %) | Conc. (wt. %) |
| --- | --- | --- | --- | --- |
| Acetic Anhydride/Acetic Acid Vapor | 10 to 60 | 20 to 50 | 25 to 45 | 30 to 40 |
| Ketene | 0.01 to 10 | 0.05 to 10 | 0.1 to 10 | 1 to 15 |
| Decomposition Gas | 40 to 80 | 45 to 75 | 50 to 80 | 50 to 70 |

The decomposition gas, in some embodiments, comprises carbon monoxide, carbon dioxide, methane, ethylene, propadiene, nitrogen and other olefins and hydrocarbons, and mixtures thereof.

As indicated above, the contacting of ketene with acetic acid, preferably, may be performed in an absorber column. The formation of acetic anhydride from the reaction between acetic acid and ketene is an exothermic reaction ($\Delta H = -63$ kJ/gmol).

In one embodiment, the absorber column is operated at lower than atmospheric pressure. For example, the top of the absorber column (vent) pressure is from 3 kPa to 100 kPa, e.g., from 30 kPa to 90 kPa, or from 40 kPa to 80 kPa, or from 40 kPa to 70 kPa, or from 50 kPa to 60 kPa. Without being bound by theory, with respect to operating temperature, there is generally a trade-off between absorber column operating temperature and its effect on acetic acid/ketene reaction kinetics, versus the vapor pressure of acetic acid. In particular, although increasing the absorber column operating temperature increases the rate of the acetic acid/ketene reaction, it also increases the amount of acetic acid and acetic anhydride that is in the vapor phase (i.e. by increasing their partial pressures). In one embodiment, the overhead operating temperature of the absorber column ranges from 10° C. to 80° C., e.g., from 35° C. to 55° C. In one embodiment, the temperature of the vent stream exiting the reactor system (e.g., absorber column) of the present invention ranges from 10° C. to 80° C., e.g., from 20° C. to 70° C. or from 30° C. to 60° C.

Secondary Reaction of Unreacted Ketene

In one embodiment, the process comprises directing at least a portion of the vent stream to a liquid ring vacuum compressor comprising a ring seal fluid comprising acetic acid. As stated above, in some embodiments, acetic acid acts as a sealer and/or as a reactant. Preferably, the unreacted ketene in the vent stream is allowed to react with acetic acid to yield supplemental acetic anhydride product.

In one embodiment, the process comprises the step of contacting the unreacted ketene in at least a portion of the vent stream with the ring seal fluid to form supplemental acetic anhydride product. As a result, overall ketene efficiency is improved. For example, the overall ketene efficiency may be at least 95%, e.g., at least 97%, at least 98%, at least 99%, at least 99.5%, or at least 99.99%. In preferred embodiments, the overall ketene efficiency is 99.5%, meaning that only approximately 0.5% of the ketene fed to the system leaves as unreacted ketene.

In one embodiment, the process maintain a ring seal fluid composition at a minimum acetic anhydride concentration level such that the amount of diketene formed in the liquid ring seal vacuum compressor is kept at a minimum.

A liquid ring stream exiting the liquid ring vacuum compressor comprises a supplemental acetic anhydride product. In one embodiment, the liquid ring stream exiting the liquid ring vacuum compressor comprises acetic anhydride. In one embodiment the liquid ring stream exiting the liquid ring vacuum compressor comprises acetic acid, and/or decomposition gas.

Exemplary compositional data for the stream exiting the liquid ring vacuum compressor are shown below in Table 5. Components other than those listed in Table 5 may also be present in the exit stream from the liquid ring vacuum compressor. For example, the exit stream may also comprise acetone and acetonitrile.

TABLE 5

COMPOSITIONS IN STREAM EXITING THE LIQUID RING VACUUM COMPRESSOR

| Component | Conc. (wt. %) | Conc. (wt. %) | Conc. (wt. %) | Conc. (wt. %) |
| --- | --- | --- | --- | --- |
| Acetic Anhydride | 20 to 95 | 25 to 80 | 30 to 70 | 35 to 65 |
| Acetic Acid | 20 to 95 | 25 to 80 | 30 to 70 | 35 to 65 |
| Decomposition Gas | 0.1 to 10 | 0.5 to 8 | 0.8 to 5 | 1 to 3 |
| Ketene | 0.01 to 1.0 | 0.01 to 0.6 | 0.1 to 0.5 | 0.1 to 0.4 |

In some embodiments, the liquid ring stream exiting the liquid ring vacuum compressor may be further processed. In one embodiment, the process may further comprise a step of separating the liquid ring stream exiting the liquid ring vacuum compressor to form a recycle stream comprising acetic acid and a decomposition gas stream. In one embodiment, the liquid ring product stream exiting the liquid ring vacuum compressor is directed to a seal fluid vessel (knockout pot) to effect the separation into a recycle stream and a decomposition gas stream. In some embodiments, decomposition gas is separated from an acetic acid/acetic anhydride mixture entering the seal fluid vessel.

In some embodiments, at least a portion of the recycle stream comprising acetic acid is recycled to back to the liquid ring vacuum compressor to supply additional acetic acid to the compressor. In some embodiments, at least a portion of the recycle stream comprising acetic acid is recycled back to the reaction unit. In some embodiments where at least a portion of the recycle stream is recycled to the reaction unit, e.g., the absorber column.

In some embodiments, at least a portion of the recycle stream is recycled back to the liquid ring vacuum compressor. In some embodiments, at least a portion of the recycle stream is recycled back to the reaction unit. For some embodiments, any one of the above-described recycle streams of the inventive process (e.g., acetic acid recycle stream fed to the compressor, acetic anhydride recycle stream fed to the reactor) may utilize a brine cooled heat exchanger to cool the recycle stream.

Exemplary compositional data for the acetic acid/acetic anhydride recycle stream are shown below in Table 6. Components other than those listed in Table 6 may also be present in the recycle stream.

TABLE 6

LIQUID RECYCLE STREAM COMPOSITIONS

| Component | Conc. (wt. %) | Conc. (wt. %) | Conc. (wt. %) | Conc. (wt. %) |
| --- | --- | --- | --- | --- |
| Acetic Anhydride | 20 to 95 | 25 to 80 | 30 to 70 | 35 to 65 |
| Acetic Acid | 20 to 95 | 25 to 80 | 30 to 70 | 35 to 65 |
| Acetone | 0.01 to 15 | 1 to 12 | 2 to 10 | 5 to 9 |
| Acetonitrile | 0.01 to 15 | 1 to 12 | 2 to 10 | 5 to 9 |

The process according to one embodiment of the present invention will now be described in relation to FIG. 1, which is a flow diagram depicting process 100 for producing acetic anhydride according to one embodiment of the present invention. Process 100 comprises primary reaction zone 101, purification zone 102, and secondary reaction zone 103. Reaction zone 101 comprises reaction unit 104. Purification zone 102 comprises a distillation unit 105, e.g., a distillation column. In some embodiments, secondary reaction zone 103 comprises both reaction and separation equipment.

Figure 1:
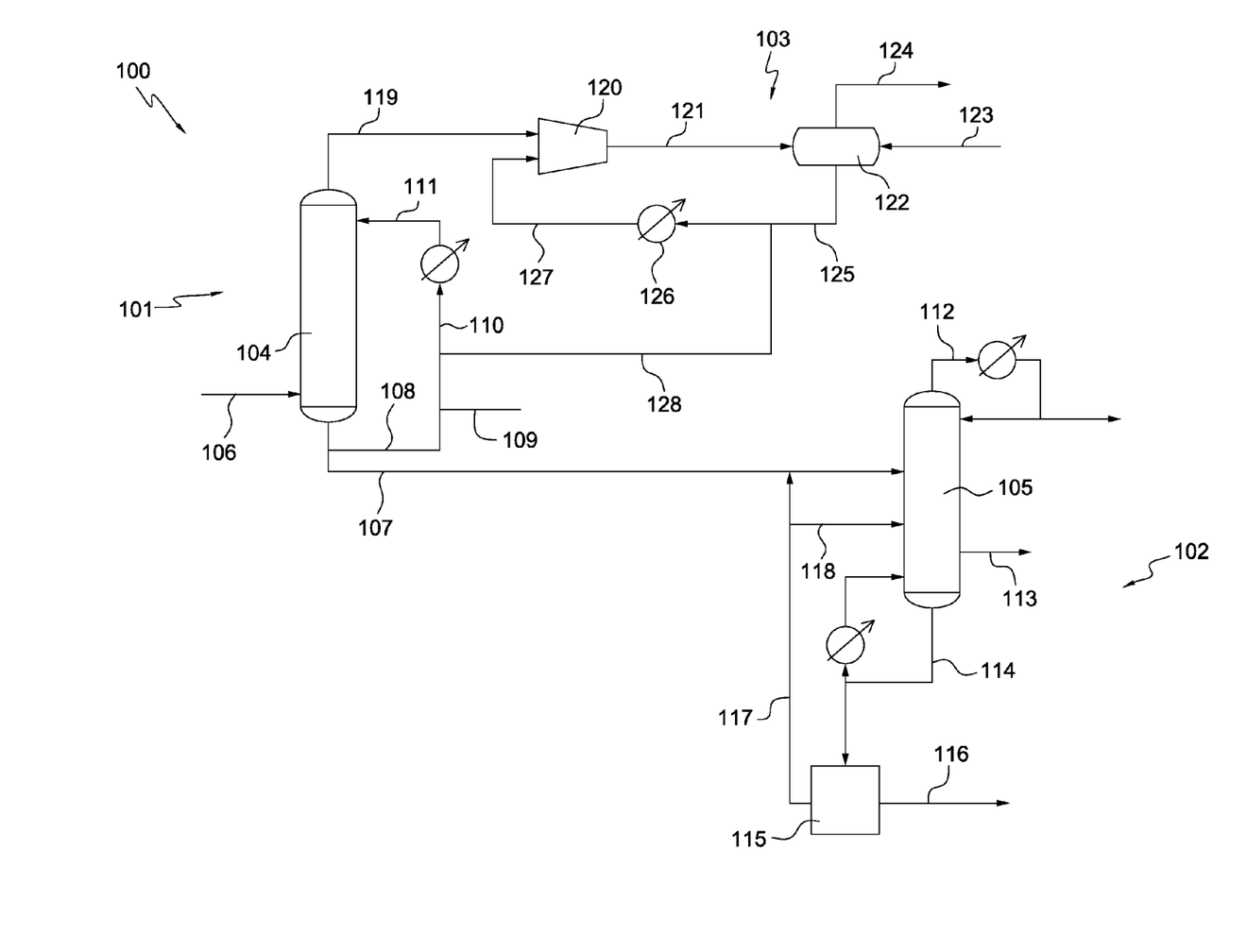
FIG. 1 is a process flowsheet showing an acetic anhydride reactor system in accordance with an embodiment of the present invention.

With reference to FIG. 1, ketene is fed to reaction unit 104 via line 106. Although not illustrated, acetic acid may also be directly fed or combined and jointly fed to the reaction unit 104 via stream 106 as shown in FIG. 1. The temperature of ketene feed stream 106 is preferably from −5° C. to 25° C., e.g., from 0° C. to 15° C., or from 5° C. to 10° C. In preferred embodiments, reaction unit 104 comprises an absorber, although other suitable reaction units may be employed to facilitate the ketene/acetic acid reaction.

In reaction unit 104, acetic acid and ketene are reacted to produce a crude acetic anhydride product stream, which exits reaction unit 104 via line 107. Although FIG. 1 shows the crude product stream being withdrawn from the bottom of reaction unit 106, the crude product stream may be withdrawn from any portion of reaction unit 104. Exemplary composition ranges for the crude product stream are shown in Table 1 above.

At least a portion of crude acetic anhydride product stream may be recycled to reaction unit 106 via line 108. In one embodiment, line 108 may be combined with acetic acid and returned to reaction unit 104. For example, line 108 may be combined with optional acetic acid feed 109 and directed to reaction unit 104. As another example, line 108 may be combined with a recycle stream, e.g., a recycle stream from secondary reaction zone 103 and directed to reaction unit 104. Resultant combined stream 110 may then be fed to heat exchanger, e.g., cooling water or a brine cooled heat exchanger 107 prior to being re-introduced to reaction unit 104 via line 111.

Crude acetic anhydride in line 107 may be fed to purification zone 102 to recover substantially pure acetic anhydride. In one embodiment, crude acetic anhydride in line 107 may be introduced directly to distillation column 105 as shown in FIG. 1. Preferably, the crude acetic anhydride in line 107 is in liquid form. In an embodiment, the crude liquid acetic anhydride may be heated before feeding to the distillation column. Distillation column 105 separates the crude acetic anhydride into distillate stream 112, sidedraw 113, and residue 114. Exemplary composition ranges for the various streams are shown in Table 2 above. Distillate stream 112 comprises light ends components and may be refluxed as shown. The light ends components may be removed from the system or recycled to another system.

Sidedraw 113 comprises substantially pure acetic anhydride, e.g., great than 98 wt. % acetic anhydride.

Residue stream 114 comprises acetic anhydride, acetic acid and heavy ends components, such as propionic acid, acetic-propionic anhydride, propionic anhydride, acetaldehyde, diketene, acetamide, diacetamide, acetonitrile, ethylidene diacetate, and 1,1-methanediol diacetate. Residue stream 114 may be boiled up as shown. To further recover acetic anhydride, heavy ends may be removed from residue stream 114 and the recovered acetic anhydride may be returned to distillation column 105. As shown in FIG. 1, residue stream 114 may be fed to heavy ends removal system 115. In one embodiment, heavy ends removal system 115 may comprise at least one distillation step. In an embodiment, other heavy ends removal systems may be used, such as multi-evaporation steps and corresponding equipment designed for concentration of solids and/or viscous mixtures containing high boiling point components. In one embodiment, the equipment designed to concentrate high-boiling components and to recover acetyls, e.g., acetic anhydride and acetic acid, could utilize single-stage evaporators or evaporators equipped with fractional distillation capabilities, e.g., column section with trays or packing. In one embodiment, the heavy-end removal systems are operated at reduced pressure. Heavy ends removal system 115 separates residue stream 114 into heavy ends stream 116 and recovered acetic anhydride stream 117. Heavy ends stream 116 may be removed from the purification system or recycled to a different system. Exemplary composition ranges for the heavy ends streams are shown above in Table 3.

As shown in FIG. 1, recovered acetic anhydride stream 117 may be returned to distillation column 105, directly or indirectly. In one embodiment, recovered acetic anhydride stream 117 may be combined with crude acetic anhydride stream 107 and fed to distillation column 105. In one embodiment, recovered acetic anhydride stream 117 may be returned to distillation column 105 directly. For example, recovered acetic anhydride stream 118 may be fed to distillation column 105 at a point below the crude acetic anhydride stream 107 and above sidedraw 113.

Returning to the reaction unit 104, unreacted ketene from reaction unit 104 flows from the top of reaction unit 104 as an overhead vent stream via line 119. Exemplary composition ranges for the vent stream are shown above in Table 4. The vent stream 119 and the unreacted ketene therein pass to liquid ring vacuum compressor 120. Liquid ring vacuum compressor 120 comprises a ring seal fluid (not shown) comprising acetic acid. The ketene from vent stream 119 reacts with the acetic acid to form additional acetic anhydride product. At least a portion of the acetic acid in the ring seal fluid is provided by a recycle stream, e.g., a recycle stream from secondary reaction zone 103. Liquid ring vacuum compressor 120 forms supplemental product stream 121, which comprises additional acetic anhydride.

Supplemental product stream 121 exits liquid ring vacuum compressor 120. In addition to acetic anhydride, supplemental product stream 121 comprises acetic acid, decomposition gas and very small amounts of ketene (if any). Exemplary composition ranges for supplemental product stream 121 are shown in Table 5 above. Supplemental product stream 121 is directed to seal fluid vessel 122. In one embodiment, seal fluid vessel 122 is a knock-out pot. Preferably, additional acetic acid is fed to seal fluid vessel 122 via line 123. Seal fluid vessel 122 separates the contents of supplemental product stream 121 to form a decomposition gas in line 124 and an acetic acid/acetic anhydride mixture (optionally comprising trace amounts of ketene) in line 125. Although a seal fluid vessel is shown in FIG. 1, other suitable separation device(s) may be employed.

Decomposition gas exits seal fluid vessel 122 in line 124, e.g., separate from the acetic acid/acetic anhydride mixture recycle stream in line 125. Although FIG. 1 shows decomposition gas being withdrawn from the top of seal fluid vessel 122, the decomposition gas stream may be withdrawn from other portions of seal fluid vessel 122. Decomposition gas stream 124 can be further cooled to lower the dew point of this stream.

The recycle stream exits seal fluid vessel 122 via line 125. At least a portion of line 125 is fed to brine cooled heat exchanger 126. At least a portion of the cooled recycle stream exits heat exchanger 126 and is fed into liquid ring vacuum compressor 120 via line 127. In one embodiment, the weight ratio of liquid in line 127 to the vaporous vent stream in line 119 is as described above. Although FIG. 1 shows recycle stream 125 being withdrawn from the bottom of seal fluid vessel 122, the liquid acetic acid/acetic anhydride mixture stream may be withdrawn from any portion of seal fluid vessel 122. At least a portion of recycle stream 125 is recycled to reaction unit 104, via line 128, which in some embodiments, may be considered a supplemental acetic anhydride product stream. In one embodiment, the weight ratio of liquid in line 111 to the vaporous ketene feed in line 106 is as described above. Exemplary composition ranges for the acetic acid/acetic anhydride recycle stream are shown in Table 6 above. The acetic acid/acetic anhydride mixture stream is recycled to reaction unit 104 in line 128, and, in one embodiment, can also be withdrawn from line 127 after the brine-cooled recirculation cooler 126.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for purifying acetic anhydride comprising the steps of:
    feeding a liquid crude acetic anhydride stream directly to a distillation column; and
    separating the liquid crude acetic anhydride stream to produce a light ends stream, a sidedraw comprising substantially pure acetic anhydride product, and a residue stream,
    wherein the distillation column operates at a pressure less than 101 kPa,
    wherein the substantially pure acetic anhydride product comprises greater than 98 wt. % acetic anhydride, has a permanganate time of greater than 10 minutes, and has an APHA color of less than 10.

2. The process according to claim 1, wherein the residue stream comprises at least 90 wt. % acetic anhydride.

3. The process according to claim 1, wherein the substantially pure acetic anhydride product is withdrawn from a point of the distillation column that is below the point at which the liquid crude acetic anhydride stream is fed.

4. The process according to claim 1, further comprising:
feeding at least a portion of the residue stream to a heavy ends removal system to produce a recovered acetic anhydride stream; and
feeding the recovered acetic anhydride stream to the distillation column.

5. The process according to claim 4, wherein at least a portion of the recovered acetic anhydride stream is fed directly to the distillation column and/or combined with the crude acetic anhydride stream.

6. The process according to claim 4, wherein the recovered acetic anhydride stream comprises at least 95 wt. % acetic anhydride.

7. The process according to claim 4, wherein the heavy ends removal system comprises at least one distillation apparatus.

8. The process according to claim 1, wherein the process further comprises heating the liquid crude acetic anhydride stream.

9. The process according to claim 1, wherein the pressure in the distillation column is from 20 kPa to 101 kPa.

10. The process according to claim 1, wherein the pressure in a top portion of the distillation column is from 20 kPa to 87 kPa.

11. The process according to claim 1, wherein the distillation column operates at a temperature less than 150° C.

12. The process according to claim 1, wherein the distillation column operates at a temperature from 100° C. to 150° C.

13. The process according to claim 1, wherein the substantially pure acetic anhydride product comprises greater than 99% acetic anhydride.

14. The process according to claim 1, wherein the substantially pure acetic anhydride product has a permanganate time of greater than 30 minutes.

15. The process according to claim 1, wherein the product acetic anhydride stream has an APHA color number of less than 5.

16. A process for producing acetic anhydride comprising the steps of:
contacting ketene gas with acetic acid in an absorber column to produce a liquid crude acetic anhydride stream and a residual ketene stream;
feeding the liquid crude acetic anhydride stream directly to a distillation column; and
purifying the liquid crude acetic anhydride stream to produce a light ends stream, a substantially pure acetic anhydride product stream, and a residue stream,
wherein the substantially pure acetic anhydride product stream is withdrawn from the distillation column as a sidedraw,
wherein the distillation column is operated at a pressure ranging from 20 kPa to 101 kPa,
wherein the substantially pure acetic anhydride product stream comprises greater than 98 wt. % acetic anhydride, has a permanganate time greater than 10 minutes, and has an APHA color number of less than 10.

17. The process according to claim 16, further comprising:
feeding at least a portion of the residue stream to a heavy ends removal system to produce a recovered acetic anhydride stream; and
feeding the recovered acetic anhydride stream to the distillation column.

18. The process according to claim 17, wherein the substantially pure acetic anhydride product is drawn from a point lower than the point at which the liquid crude acetic anhydride stream is fed.

19. The process according to claim 17, wherein at least a portion of the recovered acetic anhydride stream is fed directly to the distillation column and/or combined with the crude acetic anhydride stream.

20. The process according to claim 17, wherein the heavy ends removal system comprises at least one distillation apparatus.

21. The process according to claim 17, wherein the recovered acetic anhydride stream comprises at least 95 wt. % acetic anhydride.

22. The process according to claim 16, further comprising:
feeding the residual ketene stream to a liquid ring vacuum compressor comprising acetic acid to produce a second crude acetic anhydride stream comprising acetic anhydride and acetic acid; and
recycling at least a portion of the second crude acetic acid stream to the absorber column.

23. The process according to claim 22, wherein at least a portion of the second crude acetic anhydride stream is recycled to the liquid ring vacuum compressor.

24. The process according to claim 22, wherein the crude acetic anhydride stream further comprises a decomposition gas and the process further comprises separating the decomposition gas from the crude acetic anhydride stream.

25. The process according to claim 16, wherein the substantially pure acetic anhydride product comprises greater than 99% acetic anhydride.

26. The process according to claim 16, wherein the substantially pure acetic anhydride product stream has a permanganate time of greater than 30 minutes.

27. The process according to claim 16, wherein the substantially pure acetic anhydride product stream comprises an APHA color number of less than 5.

28. A process for purifying acetic anhydride comprising the steps of:
feeding a liquid crude acetic anhydride stream directly to a distillation column; and
separating the liquid crude acetic anhydride stream to produce a light ends stream, a sidedraw comprising substantially pure acetic anhydride product, and a residue stream,
wherein the distillation column operates at a pressure less than 101 kPa and at a temperature less than 150° C.,
wherein the substantially pure acetic anhydride product comprises greater than 98 wt. % acetic anhydride and has an APHA color of less than 10.

* * * * *